United States Patent [19]

Olson et al.

[11] Patent Number: 5,281,753
[45] Date of Patent: Jan. 25, 1994

[54] PROCESS FOR THE SELECTIVE HYDROGENATION AND ISOMERIZATION OF HYDROCARBONS

[75] Inventors: Bruce A. Olson, Reston, Va.; Asmund A. Boyum, Brooklyn, N.Y.

[73] Assignee: Engelhard Corporation, Iselin, N.J.

[21] Appl. No.: 871,881

[22] Filed: Apr. 21, 1992

[51] Int. Cl.⁵ .............................................. C07C 5/05
[52] U.S. Cl. ................................... 585/259; 585/260
[58] Field of Search ............................. 585/259, 260

[56] References Cited

U.S. PATENT DOCUMENTS

| | | |
|---|---|---|
| 2,993,855 | 7/1961 | Fear . |
| 3,215,750 | 11/1965 | Benesi . |
| 3,373,219 | 3/1965 | Kronig et al. |
| 3,485,887 | 12/1969 | Kronig et al. . |
| 3,531,545 | 9/1970 | Garner et al. . |
| 3,662,015 | 5/1972 | Komatsu et al. . |
| 3,674,886 | 7/1972 | Komatsu et al. . |
| 3,674,888 | 7/1972 | Derrien et al. . |
| 3,723,560 | 3/1973 | Gleim et al. . |
| 3,764,633 | 10/1973 | Garner et al. . |
| 3,947,510 | 3/1976 | Morelli et al. . |
| 4,132,745 | 1/1979 | Amigues et al. . |
| 4,209,655 | 6/1980 | Mitsche et al. . |
| 4,260,840 | 4/1981 | Puls et al. . |
| 4,271,323 | 6/1981 | Durand et al. . |
| 4,312,741 | 1/1982 | Jacquin . |
| 4,409,410 | 10/1983 | Cosyns et al. . |
| 4,469,907 | 9/1984 | Araki et al. . |
| 4,704,492 | 11/1987 | Nemet-Mavrodin ............... 585/259 |
| 4,716,256 | 12/1987 | Johnson et al. . |
| 4,960,960 | 10/1990 | Harrison et al. . |
| 4,995,961 | 2/1991 | Hays et al. . |

FOREIGN PATENT DOCUMENTS 1126848  9/1968  United Kingdom .

OTHER PUBLICATIONS

Boitiaux et al, "Newest Hydrogenation Catalysts", Hydrocarbon Processing, Mar. 1965 p. 51.
Eleazar et al, "Hydro–isomerization of C₄S", Hydrocarbon Processing, May 1979 p. 112.
Heck et al, "Better Use Of Butenes For High–Octane Gasoline", Hydrocarbon Processing, Apr. 1980.
Furukawa et al, "Study On The Selective Hydrogenation ... (Part 1)", Bul. of Jap. Pet. Inst, May 1973.
Furukawa et al, "Study On The Selective Hydrogenation ... (Part 2)", Bul. of Jap. Pet. Inst, May 1973.
Furukawa et al, "Study On The Selective Hydrogenation ... (Part 3)", Bul. of Jap. Pet. Inst, May 1973.

*Primary Examiner*—Asok Pal

[57] ABSTRACT

A process for the selective hydrogenation and simultaneous isomerization of hydrocarbons in a feed stream (12) containing a mixture of hydrocarbons of varying degrees of unsaturation and having 4 or more carbon atoms. The process comprises contacting the mixture with hydrogen gas under hydrogenating and isomerizing conditions in the presence of a suitable catalyst (2, 3, and 4) in a multistage packed bed catalytic reactor (1). The process comprises supplying the hydrogen gas (20) in increasing molar ratio amounts relative to the remaining unreacted diolefin concentration in at least three points (24, 26 and 28) spaced apart along the flow direction of the feed stream through the reactor.

15 Claims, 5 Drawing Sheets

PROCESS FOR THE SELECTIVE HYDROGENATION AND ISOMERIZATION OF HYDROCARBONS

BACKGROUND OF THE INVENTION

1. Field of the Invention

This invention is concerned with a process for the selective hydrogenation and simultaneous isomerization of a hydrocarbon feed stream containing a mixture of hydrocarbons of varying degrees of unsaturation and having 4 or more carbon atoms therein. The process comprises contacting the hydrocarbon feed stream with hydrogen gas under hydrogenating and isomerizing conditions in the presence of a suitable catalyst in a multi-stage packed bed catalytic reactor.

2. The Related Art

The selective hydrogenation and isomerization of hydrocarbon mixtures containing hydrocarbons with olefinic unsaturation is well-known in the art.

U.S. Pat. No. 3,485,887 is directed to the hydrogenation of $C_4$-hydrocarbon fractions containing n-butene-1 and butadiene by passing such into contact with a hydrogenation catalyst which is a metal of the Group V-VIII of the Periodic System in the presence of a hydrogen atmosphere. The product which is produced is stated to be high in n-butene and poor in butadiene content. The Patent states that the improvement of simultaneously isomerizing n-butene-1 in the fractions and produced in the hydrogenation to n-butene-2, comprises passing the $C_4$-hydrocarbon mixture in the liquid state downwardly over a fixed bed hydrogenation catalyst in a hydrogen atmosphere at an inlet temperature of the $C_4$-hydrocarbon mixture of about 10° to 35° C. and at an outlet temperature of the hydrogenated and isomerized product of 60° to 90° C.

U.S. Pat. No. 3,764,633 relates to a process and catalyst for isomerizing olefinic hydrocarbons while simultaneously hydrogenating polyolefinic hydrocarbons. Specifically, the Patent describes a process for the catalytic isomerization of monoolefinic hydrocarbons having a terminally-positioned double bond, the hydrocarbons containing at least four carbon atoms and being contained in a feedstream. The process comprises contacting a catalyst active for the isomerization of monoolefinic hydrocarbons with carbon monoxide to substantially deactivate the catalysts. The deactivated catalyst is then contacted with hydrogen to activate the catalyst for monoolefinic hydrocarbon isomerization. The activated catalyst is then contacted with a feedstream comprising the monoolefinic hydrocarbons to isomerize the same.

In column 4, line 68 through column 5, line 2 of this Patent, it is stated that the process may be carried out while introducing hydrogen into the reaction at a plurality of points within the reaction zone. Also, in column 7, lines 55 to 64 of the Patent, it is stated that distribution of the hydrogen introduced to the plurality of injection points will vary with the nature of the feedstock and the configuration of the bed. Generally, this Patent states that if two beds are employed, from about 95 to about 75 percent of the total hydrogen introduced will be added to the first bed, the remainder being added to the second bed. If more than two beds are employed, the addition of hydrogen will be in decreasing amounts to successive beds (column 7, lines 56–64).

U.S. Pat. No. 4,132,745 relates to a process for isomerizing 1-butene to 2-butene by contacting the 1-butene at a temperature from 50° to 140° C., in the presence of hydrogen, with an isomerization catalyst containing a Noble metal from Group VIII of the Periodic Classification of Elements. The catalyst is pretreated by contacting with a sulfur compound and then with hydrogen. The Patent states that the process described therein provides for the isomerization of 1-butene at a lower temperature than the prior processes and, accordingly, results in a more complete conversion to 2-butene.

U.S. Pat. No. 4,260,840 concerns selectively hydrogenating butadiene to butene in a $C_4$ fraction containing at least 30 weight percent butene-1. Specifically, it is stated that a butene stream can be hydrogenated that contains a substantial amount of butene-1 of at least 30 percent and contains butadiene as an impurity, and which may contain other impurities. Such stream is hydrogenated by treatment with hydrogen under controlled conditions to convert the butadiene to butene while minimizing losses of butene-1 due to isomerization of butene-1 to butene-2 and hydrogenation of butene-1 and butene-2 to butane.

U.S. Pat. No. 4,312,741 describes a process for the catalytic hydrogenation of a hydrocarbon feedstock. The apparatus comprises a reactor unit having fluidized catalyst beds in a plurality of hydrogen inlet distribution fixtures. The separate beds may be contained within a single vessel or in separate vessels. The disclosure of this Patent does not allege the utility of the invention with respect to hydrogenating dienes or to isomerization, rather general utility for hydrogenation conversion reactions is alleged (column 1, lines 5–22 and column 5, lines 1–23). The multiplicity of fluidized beds is intended to improve catalyst mobility (column 2, lines 18–34).

U.S. Pat. No. 4,960,960 discloses a hydrogenation process utilizing first and second hydrogenation zones, wherein each may include two or more beds of catalyst, and each of which may be supplied with a hydrogen-containing feed gas (column 2, lines 43 through column 3, line 18; column 5, lines 18–25 and lines 45–48). The process described is not specific to any particular hydrogenation reaction (column 3, line 48 to column 5, line 17).

U.S. Pat. No. 4,469,907 is directed to a method of selectively hydrogenating highly unsaturated hydrocarbons by contacting a mixture of hydrocarbons of low unsaturated degree having four or more carbon atoms containing the highly unsaturated hydrocarbons into contact with hydrogen. The hydrogenation is conducted in the presence of a catalyst using a fixed bed reaction vessel. The process comprises supplying the hydrogen gas in a state of plural splits along the flow direction of the fixed bed reaction vessel. Also, the Patent states that the rate of flow of hydrogen gas in the second split or later split or splits along the flow direction of the fixed bed reaction vessel is 5 to 100% of the previous split (column 2, lines 43 to 48).

The Patent further states that the advantage of the invention therein is that a method is provided of selectably hydrogenating highly unsaturated hydrocarbons only, without being accompanied by isomerization of olefins (column 3, lines 46 to 51).

SUMMARY OF THE INVENTION

Generally, the present invention provides a process for selectively hydrogenating and simultaneously isomerizing hydrocarbons in a feed stream containing a mixture of hydrocarbons of varying degrees of unsaturation and having 4 or more carbon atoms. This process is carried out by introducing the hydrogen gas into the hydrocarbon stream at three or more locations spaced apart along the flow path of the hydrocarbons through the catalyst bed, with increasing amounts of hydrogen relative to unreacted diolefin being introduced in each subsequent stage, i.e., increasing hydrogen to diolefin molar ratio.

More specifically, in accordance with the present invention, there is provided a method for the selected hydrogenation and simultaneous isomerization of a hydrocarbon feed stream containing a mixture of hydrocarbons comprising varying degrees of unsaturation and having 4 or more carbon atoms. The hydrocarbons of varying degrees of unsaturation include hydrocarbons with high degrees of unsaturation such as the diolefins, butadiene and pentadiene and hydrocarbons with low degrees of unsaturation such as the olefins, butenes and pentenes. According to the process of this invention, the highly unsaturated hydrocarbons of the present invention are hydrogenated while the hydrocarbons of low unsaturation are simultaneously isomerized. In the process of this invention the hydrocarbon feed stream containing the mixture of hydrocarbons of varying degrees of unsaturation is contacted under hydrogenating and isomerizing conditions with hydrogen gas in the presence of a suitable catalyst in a multi-stage packed bed catalytic reactor. Hydrogen gas is added in an increasing molar ratio relative to the remaining unreacted diolefin to the reactor at a plurality of points spaced apart along the flow direction of the feed stream through the reactor. The hydrogen gas is added to at least three points spaced apart in the reactor.

A further aspect of the invention comprises adding the hydrogen gas to a multi-stage packed bed catalytic reactor in at least three points spaced apart in increasing hydrogen to diolefin molar ratio. Preferably this ratio is a sub-stoichiometric hydrogen to diolefin molar ratio, in stoichiometric hydrogen to diolefin molar ratio and in amounts in excess of the stoichiometric amount of hydrogen required to convert all remaining diolefin to olefin along the flow direction of the feed stream through the reactor.

The process of the present invention advantageously results in improved selectivity of diolefin versus olefin hydrogenation and isomerization of, for example, butene-1 to butene-2. This is achieved by staging hydrogen addition to at least three points spaced apart in a multistage packed bed catalytic reactor. This is in contrast to the prior art processes wherein hydrogen gas is generally added initially with the hydrocarbon feed stream.

The process of the present invention is further advantageous in favoring diolefin (for example, butadiene or pentadiene) over olefin reaction (butene-1 or pentene-1 by avoiding conditions where the catalyst surface is flooded with an excess of hydrogen (as when the hydrogen gas is added to the reactor initially with the hydrocarbon feed stream) which can be subsequently consumed by undesired reaction with olefins. The favored diolefin reaction is achieved by staging the addition of hydrogen gas in an increasing hydrogen to diolefin molar ratio to points spaced apart along the flow direction of a multistage packed bed catalytic reactor.

Another advantage of the process of this invention, is that the isomerization may be controlled to obtain a predominant amount of the isomer of choice. For example, if butene-2 is desired, the isomerization of butene-1 to butene-2 can be controlled by the process of this invention, with the added benefit of consuming less hydrogen for the undesired saturation of olefin to paraffin.

DETAILED DESCRIPTION OF THE INVENTION AND PREFERRED EMBODIMENTS THEREOF

Figure 1:
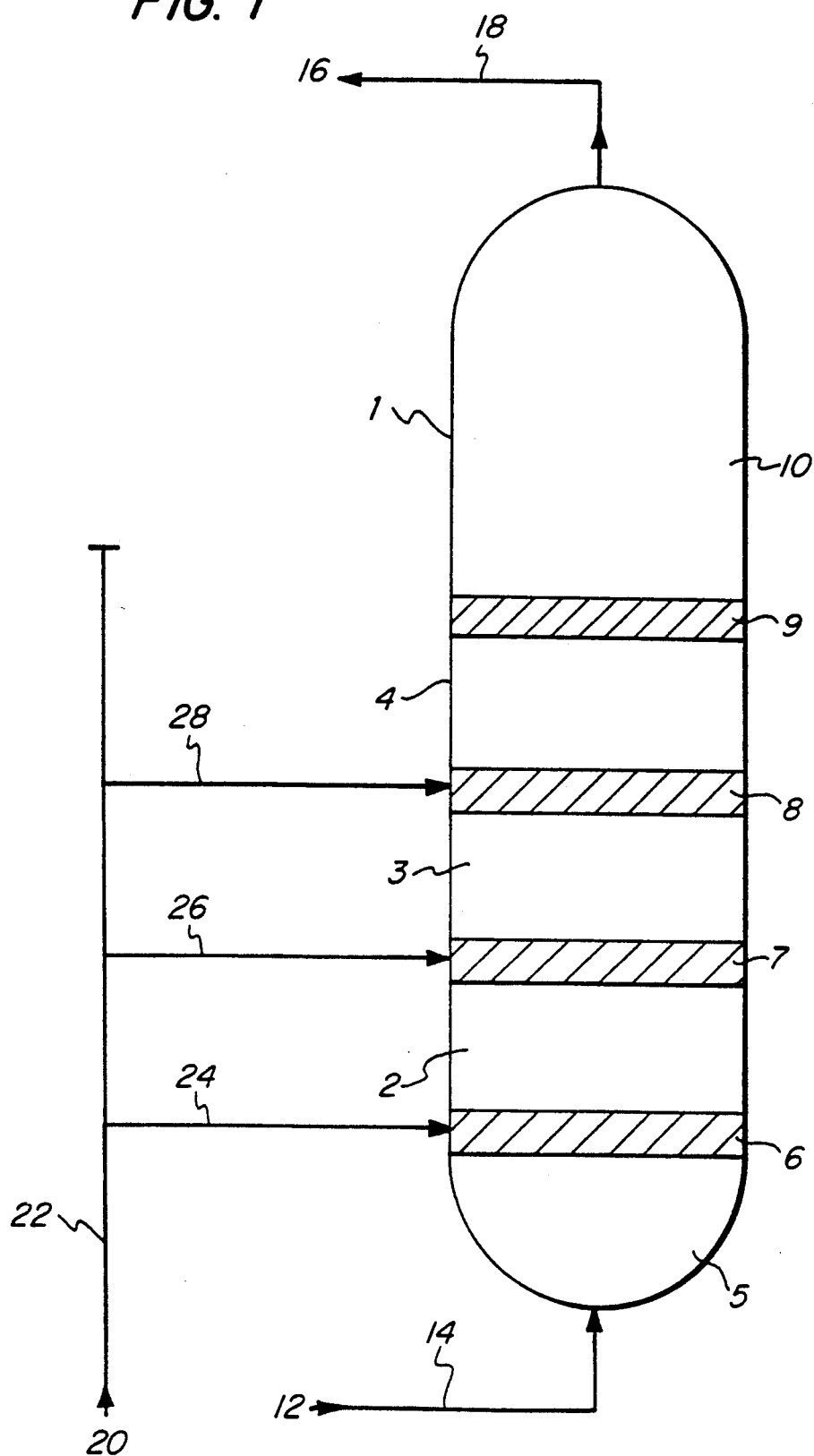
FIG. 1 is a diagrammatic illustration, with the multistage packed bed catalytic reactor shown in cross section, of an embodiment of the invention depicting the addition of hydrogen gas to a plurality of points spaced apart along the flow direction of a hydrocarbon feed stream through the reactor.

In one embodiment of the process of this invention, a hydrocarbon feed stream containing a mixture of hydrocarbons of varying degrees of unsaturation and having 4 or more carbon atoms is selectively hydrogenated and simultaneously isomerized. The hydrocarbon feed stream is contacted with hydrogen gas under hydrogenating and isomerizing conditions in the presence of a suitable catalyst in a multi-stage packed bed catalytic reactor wherein the hydrogen gas is supplied to the reactor in increasing amounts in at least three points spaced apart along the flow direction of the feed stream through the reactor.

In the process of this invention, the hydrocarbon feed stream containing a mixture of hydrocarbons of varying degrees of unsaturation and having 4 or more carbon atoms generally contains from 0 to about 10 percent by volume of hydrocarbon with high degrees of unsaturation and from about 10 to about 100 percent by volume of hydrocarbons with low degrees of unsaturation. The preferred hydrocarbon feed stream contains a mixture of hydrocarbons comprising varying degrees of unsaturation and having 4 to 6 carbon atoms. A preferred mixture of hydrocarbon comprises butadiene and butenes and/or pentadiene and pentenes.

The process of this invention is carried out at a pressure of from about 100 to about 500 psig, preferably from about 200 to about 400 psig.

The process of this invention is carried out at temperatures of from about 30° to about 300° C., preferably from about 50° to about 100° C. The inlet temperature of the reactor is generally from about 30° to about 50° C.

The catalyst which may be used in the process of this invention comprises at least one Noble metal selected from Group VIII, i.e., ruthenium, rhodium, palladium, osmium, iridium, and/or platinum, on a carrier. Palladium is the preferred metal. Any one of the usual carriers may be used, for example, alumina, silica-alumina, carbon and the like, with the preferred carrier being alumina. The preferred catalyst comprises a composition and contains from about 0.01 to about 2 percent by weight of palladium on an alumina carrier.

The hydrogen gas preferably contains a major amount of hydrogen and at most a minor amount of one or more inert gases.

The hydrogen gas in the process of this invention is supplied in increasing amounts to the multi-stage packed bed catalytic reactor at a plurality of points spaced apart. Preferably, the hydrogen gas is supplied to the reactor in increasing amounts in at least three points spaced apart along the flow direction of a hydrocarbon feed stream added to the reactor. The hydrogen gas is added in increasing amounts starting with a sub-stoichiometric amount and then increasing to a stoichiometric amount, and then increasing to an excess of stoichiometric amount relative to the unreacted diolefin concentration at the point of hydrogen introduction. These amounts of hydrogen gas are selected based upon the amounts of hydrocarbons in the feed stream.

The process of this invention may be carried out in a liquid phase, a vapor phase, or a vapor-liquid mixed phase. The reaction in a liquid or vapor-liquid mixed phase is preferred in carrying out the process of this invention.

In the practice of the process of this invention, the hydrocarbon feed stream may be added to the inlet of a multi-stage packed bed catalytic reactor. The reactor is preferably an upflow packed bed catalytic reactor. The reactor comprises at least three reaction zones or stages. Each zone or stage may each include at least one catalyst bed. Conveniently, however, each zone or stage comprises a single catalyst bed. Thus, in a preferred process the reaction zones comprise respective beds of catalyst mounted one above another within the reactor. However, the multi-stage packed bed catalytic reactor may comprise three or more packed bed catalytic reactors connected with each other in series. In the practice of the process of this invention, the hydrogen gas may be added to each reaction zone or stage of the reactor from a single source wherein the hydrogen gas is split to enter each zone or stage. Alternatively, the hydrogen gas may be supplied to each reaction zone from independent or separate sources.

Referring to FIG. 1, this depicts a multi-stage packed bed catalytic reactor 1 containing catalyst beds 2, 3 and 4. The reactor 1 also contains packed inert materials 6, 7, 8 and 9, which may be, for example, silica. Reactor 1 also contains feed distributor 5. Void space 10 is also present within reactor 1. The hydrocarbon feed stream 12 flows into reactor 1 through line 14. Product 6 leaves reactor 1 through line 18. Hydrogen gas 20 flows through line 22, is split and enters reactor 1 via lines 24, 26 and 28. Flow control valves which control the flow of hydrogen gas and the hydrocarbon feed stream into reactor 1 have not been depicted.

This Figure illustrates a preferred embodiment of this invention in that the hydrogen gas 20 is added through line 22 and is split and added to reactor 1 through lines 24, 26 and 28 in increasing amounts to the packed inert materials 6, 7 and 8.

The following Examples demonstrate the efficacy of certain embodiments of the present invention.

EXAMPLE AND COMPARATIVE EXAMPLES A AND B

Hydrocarbon feed streams containing butadiene, butane and butenes were contacted with hydrogen in a multi-stage packed bed catalytic reactor under the indicated operating conditions as set forth in TABLES A, B and C.

In Comparative Example A, butadiene was saturated from a concentration of 42628 ppm (TABLE B) in a butene-1-containing feed stream to 284 ppm in the product (TABLE B). Butene-1 gain (product minus feed) was 22931 (TABLE C) ppm but n-butane gain (reflective of undesired n-butene saturation losses to n-butane with attendant hydrogen gas consumption) was 19413 ppm (TABLE C). Butene-1 approach to equilibrium was 32.89% (TABLE C).

In Comparative Example B, the hydrogen gas was increased to increase the extent of butadiene removal and butene-1 isomerization to 38 ppm in the product (TABLE B) and 60.17% butene-1 approach to equilibrium isomerization (TABLE C). However, the large hydrogen excess was consumed in olefin saturation. There was a resulting loss of n-butenes of 2360 ppm (TABLE C) and an overall loss of 87540 ppm hydrogen (44950 ppm n-butane gain), (TABLE C).

In the process of this invention as shown in Example 1, runs 1 to 3 can be combined in series to achieve better results with less hydrogen consumption and olefin loss. In this example, more butadiene is hydrogenated overall (46501 vs. 42344 ppm), less hydrogen is consumed (58395 vs. 61757 ppm), desired n-butene gain is greater (34609 vs. 22931 ppm) and undesired olefin losses to n-butane are less (11892 vs. 19413 ppm). Final butadiene concentration in the product stream is 24 vs. 284 ppm and butene-1 approach to equilibrium is greater than "40.84% vs. 32.89%."

The results obtained by the process of this invention as carried out by the procedure of Example 1 and the process of the prior art as carried out by the procedure of Comparative Example A are plotted in FIGS. 2-5.

Figure 2:
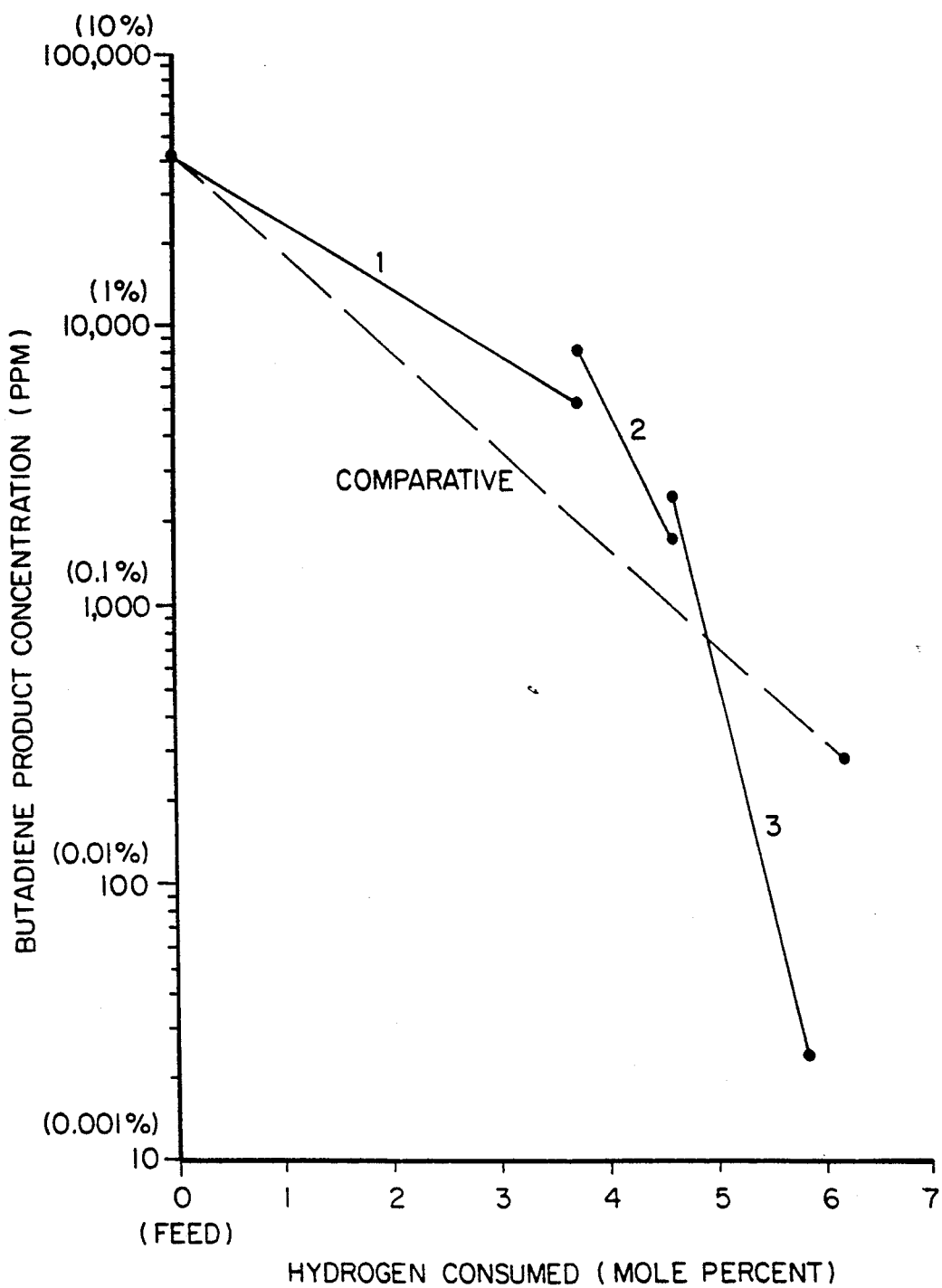
FIG. 2 is a plot showing product butadiene concentration in parts per million versus hydrogen consumption in mole percent.

FIG. 2 compares the process of this invention wherein the reaction is carried out in successive stages, i.e., stages 1, 2 and 3 and the process of the prior art (Comparative Example A) wherein the hydrogen gas is added at the initial stage of the reaction together with the hydrocarbon feed stream. The plot shows that the process of this invention, with three runs, converts more butadiene, as compared to the prior art process consuming about the same amounts of hydrogen. This is seen wherein butadiene products concentration in parts per million is plotted versus hydrogen consumption in mole percent.

Figure 3:
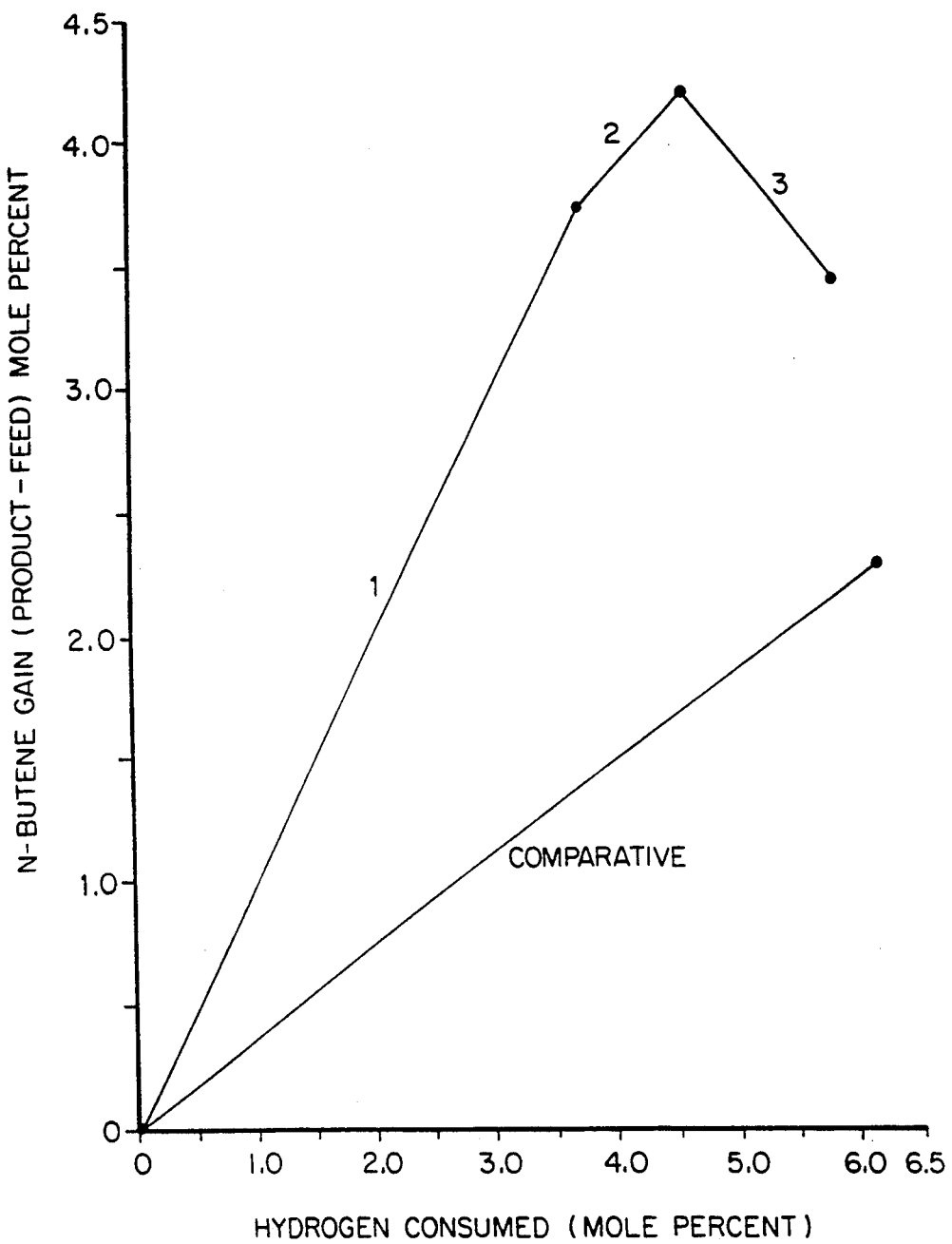
FIG. 3 is a plot showing butene gain (product minus feed) in mole percent versus hydrogen consumed in mole percent.

FIG. 3 compares the same processes and plots gain of butene-1 and butene-2 in mole percent versus hydrogen consumed in mole percent.

Figure 4:
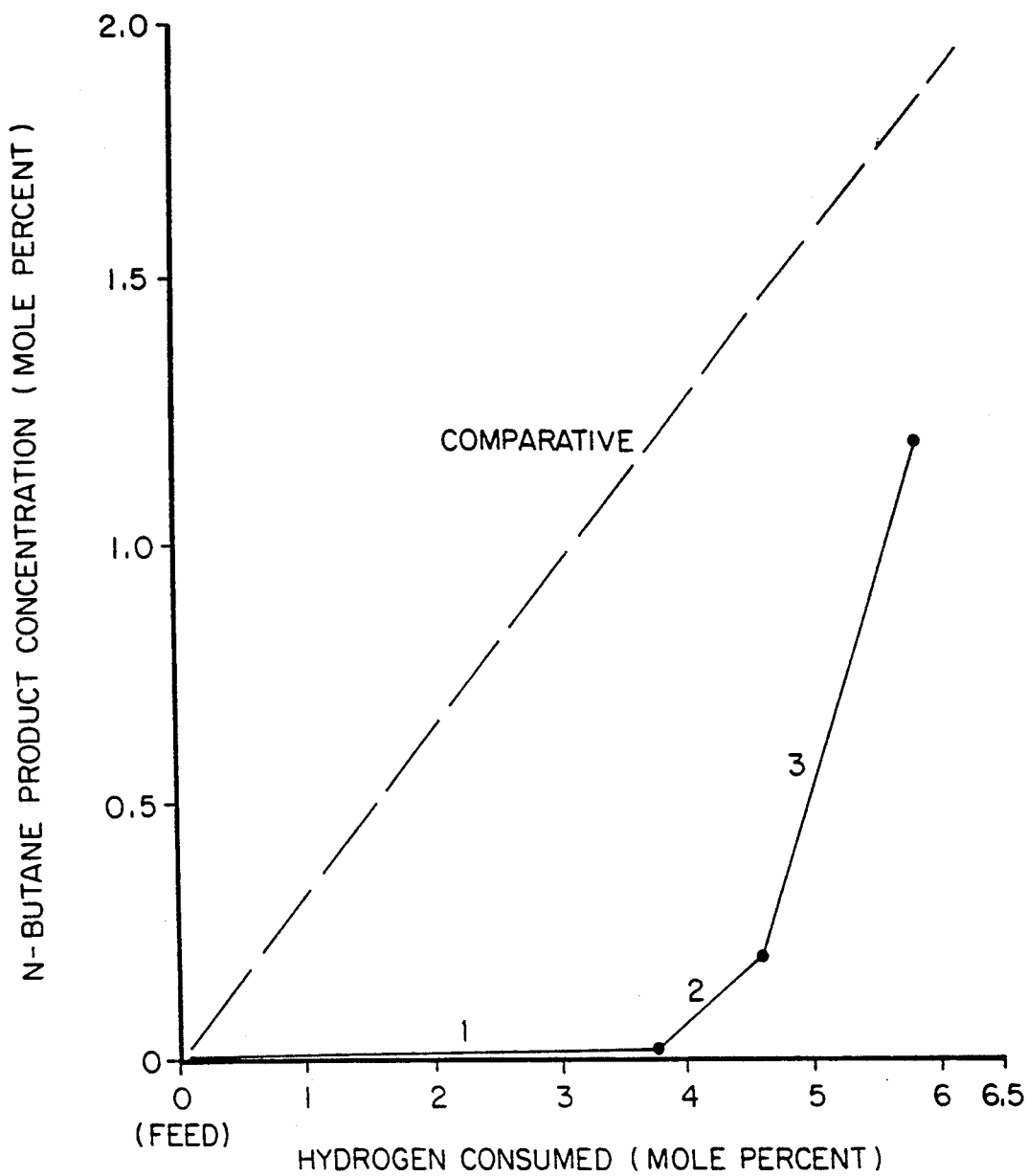
FIG. 4 is a plot showing butane product concentration in mole percent versus hydrogen consumed in mole percent.

FIG. 4 compares the same processes and plots butane product concentration in mole percent versus hydrogen consumed in mole percent. The data shows that the process of this invention produces less of the undesired butane product.

Figure 5:
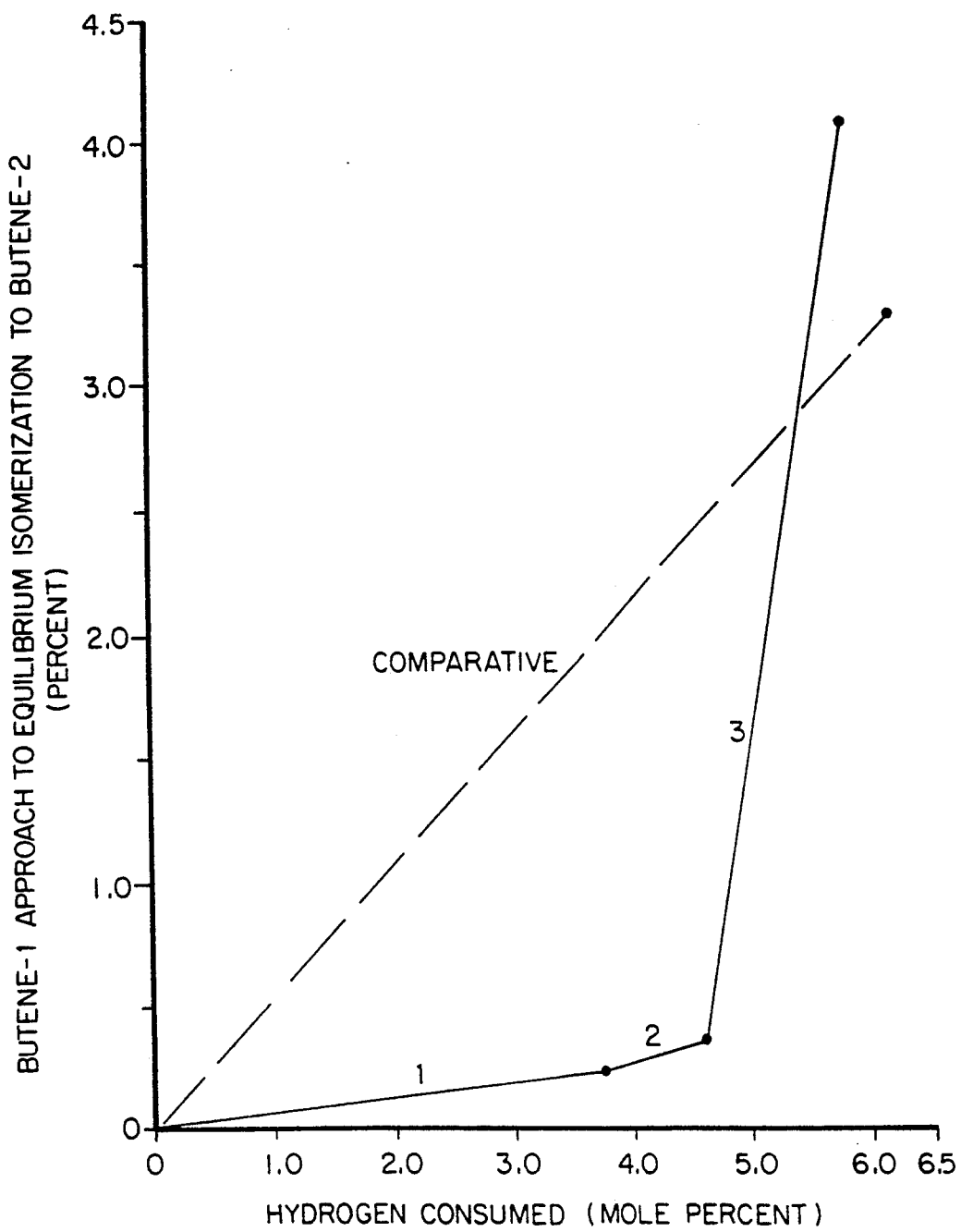
FIG. 5 is a plot showing butene-1 approach to equilibrium isomerization to butene-2 in mole percent versus hydrogen consumed in mole percent.

FIG. 5 compares the same processes and plots the percent of butene-1 isomerization to butene-2 versus hydrogen consumed in mole percent. The data shows that the process of this invention may be used to control the amount of isomerization of butene-1 to butene-2. Thus, a method is provided wherein the isomerization process may be controlled to increase the amounts of butene-1 isomerized to butene-2, with minimum undesired olefin saturation (hydrogen losses) and maximum removal of diolefin (selective hydrogenation).

TABLE A

| Ex./Run | (a) | (b) | (c) | (d) | (e) | (f) |
|---|---|---|---|---|---|---|
| 1/1 | 46 | 350 | 6.36 | 0.8896 | 38110 | −0.437 |
| 1/2 | 43 | 350 | 3.86 | 1.011 | 8420 | 0.0010 |
| 1/3 | 50 | 400 | 3.68 | 5.090 | 12624 | 1.015 |
| A | 49 | 350 | 6.04 | 1.45 | 61811 | 1.919 |
| B | 52 | 350 | 6.16 | 2.06 | 87857 | 4.525 |

(a) Temp. (°C.)
(b) Pressue (psig)
(c) WHSV = weight hourly space velocity ($Hr^{-1}$)
(d) $H_2$/BD = molar ratio of hydrogen gas to butadiene
(e) ($H_2$/HC) × $10^6$ = molar ratio of hydrogen gas to hydrocarbon (f) $\dfrac{(H_2 - BD) \times 10^2}{\Sigma \text{ olefins} + \text{diolefins}}$ = molar ratio of hydrogen gas minus butadiene × $10^2$ divided by the summation of the amounts of olefins and diolefins

TABLE B

| Ex./Run | (g) | (h) | (i) | (j) | (k) | (l) |
|---|---|---|---|---|---|---|
| 1/1 | 489 | 42841 | 5383 | 13.194 | 0.0011 | 0.1580 |
| 1/2 | 7 | 8325 | 1738 | 6.048 | 0.0071 | 0.1402 |
| 1/3 | 263 | 2480 | 24 | 17.087 | 0.0367 | 1.934 |
| A | 54 | 42628 | 284 | 30.289 | 0.1196 | 2.411 |
| B | 317 | 42620 | 38 | 43.280 | 0.285 | 5.674 |

(g) $H_2$ Prod (ppm) = hydrogen product concentration
(h) BD Feed (ppm) = butadiene feed concentration
(i) BD Prod (ppm) = butadiene product concentration
(j) $k_{BD}$ ($Hr^{-1}$) = rate constant of butadiene hydrogenation
(k) $k_B$ ($Hr^{-1}$) = rate constant of butene hydrogenation
(l) $k_I$ ($Hr^{-1}$) = rate contant of the isomerization of butene-1 to butene-2

TABLE C

| Ex./Run | (m) | (n) | (o) | (p) | (q) | (r) |
|---|---|---|---|---|---|---|
| 1/1 | 12494 | 83.528 | 150 | 2.45 | 37295 | 163 |
| 1/2 | 853 | 43.150 | 19.772 | 3.57 | 4761 | 1826 |
| 1/3 | 465 | 8.836 | 52.674 | 40.84 | −7447 | 9903 |
| A | 253 | 12.563 | 20.164 | 32.89 | 22931 | 19413 |
| B | 152 | 7.628 | 19.885 | 60.17 | −2360 | 44950 |

(m) $k_{BD}$/B = ratio of the rate constant of butadiene to butene hydrogenation
(n) $k_{BD}$/I = ratio of the rate constant of butadiene hydrogenation to butene isomerization
(o) $k_I$/B = ratio of the rate constant of isomerization to butene hydrogenation
(p) Butene-1 ATE (approach to equilibrium) (%)
(q) n-Butene Gain (Product minus Feed) ppm (desirable)
(r) n-Butane Gain (Product minus Feed) ppm (undesirable)

While the invention has been described in detail with respect to preferred embodiments thereof, it will be appreciated by those skilled in the art that, upon a reading and understanding of the foregoing, numerous variations may be made to the disclosed embodiments which variations are nonetheless believed to lie within the spirit and scope of the invention and the appended claims.

What is claimed is:

1. A process for the selective hydrogenation of diolefin hydrocarbons and simultaneous isomerization of mono-olefin hydrocarbons in a feed stream containing a mixture of hydrocarbons of varying depress of unsaturation including diolefins and having 4 or more carbon atoms, comprising contacting said mixture with hydrogen gas under hydrogenating and isomerizing conditions in the presence of a suitable catalyst in a multistage packed bed catalytic reactor which process comprises supplying said hydrogen gas to said reactor at a plurality of supply points spaced apart along the flow direction of said feed stream through said reactor, the molar ratio of hydrogen gas to unreacted diolefin at the first or starting supply point being sub-stoichiometric, and the molar ratio of hydrogen gas added to unreacted diolefin at a subsequent supply point being in excess of stoichiometric with respect to the unreacted diolefin at that point.

2. The process of claim 1 wherein said plurality of supply points comprises said first supply point, and at least a second and a third supply point spaced along the flow direction of the feed stream, and wherein the molar ratio of hydrogen gas to unreacted diolefin at the second supply point is stoichiometric and the molar ratio of hydrogen gas to unreacted diolefin at the third supply point is excess of stoichiometric, with respect to the unreacted diolefin at the respective points.

3. The process of claim 1 or claim 2 wherein said mixture of hydrocarbons comprising varying degrees of unsaturation contains 4 to 6 carbon atoms.

4. The process of claim 3 wherein said hydrocarbons of varying degrees of unsaturation comprise butadiene.

5. The process of claim 3 wherein said hydrocarbons of varying degrees of unsaturation comprise pentadiene.

6. The process of claim 3 wherein said mixture of hydrocarbons comprises butadiene and butene.

7. The process of claim 3 wherein said mixture of hydrocarbons comprises pentadiene and pentene.

8. The process of claim 1 or claim 2 which is carried out in the liquid and/or vapor-liquid mixed phase.

9. The process of claim 1 or claim 2 wherein the catalyst comprises at least one Group VIII Noble metal on a carrier.

10. The process of claim 9 wherein the catalyst is palladium on alumina.

11. The process of claim 1 or claim 2 wherein the hydrogen gas is supplied in a state of plural splits to the reactor.

12. A process for the selective hydrogenation of diolefin hydrocarbons to mono-olefin hydrocarbons and simultaneous isomerization of mono-olefin hydrocarbons in a feed stream containing a mixture of butadiene and butenes comprising contacting said mixture with hydrogen gas under hydrogenating and isomerizing conditions in the presence of a catalyst composition comprising a Group VIII Noble metal on a carrier in a multi-stage packed bed catalytic reactor, which process comprises performing the hydrogenation and isomerization process in a liquid and/or vapor-liquid mixed phase by supplying said hydrogen gas to said reactor in at least three supply points spaced apart along the flow direction of said feed stream through said reactor in molar ratio amounts starting with sub-stoichiometric at the first supply point and increasing to stoichiometric and then to excess of stoichiometric relative to any unreacted butadiene content remaining in said feed stream at successive respective supply points.

13. The process of claim 2 wherein said hydrogen gas is supplied to said reactor in increasing amounts of sub-stiochiometric, stoichiometric and amounts in excess of stoichiometric relative to the amount required to convert any remaining butadiene to butenes in three points spaced apart along the flow direction of said feed stream through said reactor.

14. A process for the selective hydrogenation of diolefin hydrocarbons and simultaneous isomerization of mono-olefin hydrocarbons in a feed stream containing a mixture of pentadiene and pentenes comprising contacting said mixture with hydrogen gas under hydrogenating and isomerizing conditions in the presence of a catalyst composition comprising a Group VIII Noble metal on a carrier in a multi-stage packed bed catalytic reactor, which process comprises performing the hydrogenation and isomerization process in a liquid and/or vapor-liquid mixed phase by supplying said hydrogen gas to said reactor in at least three supply points spaced apart along the flow direction of said feed stream through said reaction in molar ratio amounts starting with sub-stiochiometirc at the first supply point and increasing to stoichiometric and then to excess of stoichiometric relative to any unreacted pentadiene content remaining in said feed stream at successive respective supply points.

15. The process of claim 14 wherein said hydrogen gas is supplied to said reactor in increasing amounts of substoichiometric, stoichiometric and amounts in excess of stoichiometric relative to the amount required to convert any remaining pentadiene to pentenes in three points spaced apart along the flow direction of said feed stream through said reactor.

* * * * *